United States Patent [19]

Hamberger et al.

[11] 4,320,133

[45] Mar. 16, 1982

[54] PENICILLINS AND THEIR ANTIBACTERIAL USE

[75] Inventors: Helmut Hamberger; Peter Stütz; Dieter Scholz; Hans Fliri, all of Vienna, Austria

[73] Assignee: Sandoz Ltd., Basel, Switzerland

[21] Appl. No.: 119,044

[22] Filed: Feb. 6, 1980

Related U.S. Application Data

[63] Continuation-in-part of Ser. No. 3,846, Jan. 16, 1979, abandoned.

[30] Foreign Application Priority Data

Jan. 16, 1978 [SE] Sweden .................................. 413/78

[51] Int. Cl.³ ..................... A61K 31/41; A61K 31/43; C07D 499/70
[52] U.S. Cl. ................................. 424/269; 260/239.1; 424/271; 544/22; 544/28
[58] Field of Search ..................... 260/239.1; 424/271, 424/269; 544/22, 28

[56] References Cited

U.S. PATENT DOCUMENTS 3,939,150  2/1976  Murakami et al. ............... 260/239.1
4,005,075  3/1977  Yamada et al. .................. 260/239.1
4,159,268  6/1979  Curran et al. .................... 260/239.1

*Primary Examiner*—Natalie Trousof
*Assistant Examiner*—Vera C. Clarke
*Attorney, Agent, or Firm*—Gerald D. Sharkin; Robert S. Honor; Timothy G. Rothwell

[57] ABSTRACT

The invention provides novel penicillins and cephalosporins of formula I, $$R_5 \underset{R_4}{\overset{D}{\underset{B}{\bigodot}}} \overset{D}{\underset{R_3}{\parallel}} -A-NH-\underset{R_2}{\overset{|}{C}H}-CO-NH-\overset{H}{\underset{O}{\overset{|}{C}}} \overset{H}{\underset{N}{\overset{S}{\diagdown}}} \overset{}{\underset{COOR_1}{\diagup}} X \quad I$$

methods for their production and their anti-bacterial use.

9 Claims, No Drawings

PENICILLINS AND THEIR ANTIBACTERIAL USE

This application is a continuation in part of copending application Ser. No. 3,846 filed Jan. 16, 1979 which is now abandoned.

This invention provides compounds of formula I,

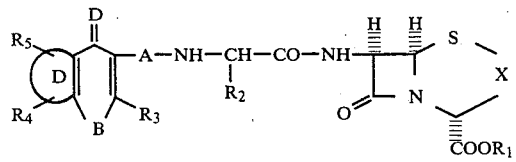

in which
R$_1$ is hydrogen or pivaloyloxymethyl,
R$_2$ is phenyl, 4-hydroxyphenyl or 1,4-cyclohexadien-1-yl,
R$_3$ is hydrogen, lower alkyl or lower alkylthio,
R$_4$ and R$_5$, which may be the same or different, are hydrogen, lower alkyl, hydroxy, lower alkoxy, carboxyl, lower alkoxycarbonyl, lower alkoxycarbonylmethyl, carboxymethyl or halogen,
A is the group

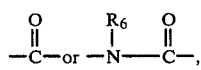

in which R$_6$ is hydrogen or lower alkyl,
B is oxygen or sulphur,
X is a group of formula IIa or IIb,

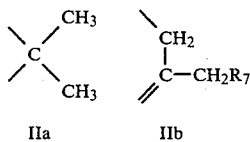

in which R$_7$ is hydrogen, acetoxy or a group of formula IIc,

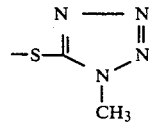

and Ring D is a 5- or 6-membered, unsaturated ring, which may contain one or more hetero atoms,
and salts of compounds of formula I, which R$_1$ is hydrogen.

The term "lower" as used herein with reference to alkyl, alkoxy and alkylthio groups means containing preferably 1 to 4, more preferably 1 to 2 carbon atoms. The term "halogen" means, unless otherwise indicated, preferably fluorine, chlorine, or bromine.

The invention also provides processes for the production of compounds of formula I, comprising
(a) reacting a compound of formula III,

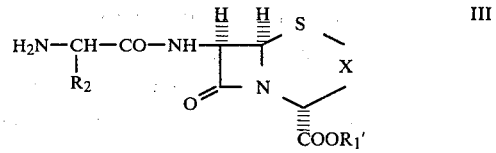

in which
R$_2$ and X are as defined above, and
R$_1'$ is hydrogen, pivaloyloxymethyl, or a carboxylic acid protecting group removable under mild conditions,
with a reactive derivative of an acid of formula IV,

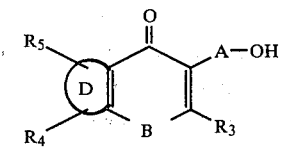

in which R$_3$, R$_4$, R$_5$, A, B and ring D are as defined above,
or, when A is CO, the free acid of formula IV, and, where R$_1'$ signifies a carboxylic acid protecting group, removing this under mild conditions, or (b) reacting a compound of formula V,

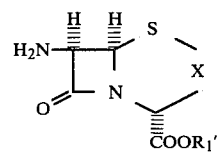

in which X and R$_1'$ are as defined above,
with a reactive derivative of an acid of formula IV,

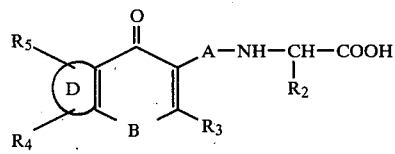

in which R$_2$, R$_3$, R$_4$, R$_5$, A, B and ring D are as defined above,
and, where R$_1'$ signifies a carboxylic acid protecting group, removing this under mild conditions.

Processes (a) and (b) may be effected in conventional manner, for example by reacting a solution or suspension of a compound of formula IV or VI, or a reactive derivative thereof, for example an acid halide, anhydride or ester, in an inert solvent, such as a cyclic ether, e.g. tetrahydrofuran, or a halogenated hydrocarbon, as methylene chloride, with a solution or suspension of the compound of formula III or V, suitably in the same solvent. When a free acid of formula IV or VI is employed, the reaction is suitably effected in the presence of a condensation agent, for example dicyclohexylcarbodiimide or carbonyldiimidazole. When R$_1'$ is a carboxylic acid protecting group, this may be any protecting group removable under mild conditions, as is conventional in the penicillin and cephalosporin field for acylation reactions, and may be removed in conventional manner, to yield compounds of formula I in which $R_1$ is hydrogen, or salts thereof.

The resulting compounds of formula I may be isolated and purified using conventional techniques. Where required, free acid forms of the compounds of formula I (i.e. $R_1 = H$) may be converted into salt forms thereof in conventional manner, and vice versa. The preferred salt forms are alkali metal salt forms. The compounds of formula I in which $R_1$ is hydrogen, and in particular salt forms thereof, more particularly alkali metal salt forms thereof may exist in the form of hydrates, to which the invention also extends.

The starting materials of formula IV are, at least in part, new. Ethyl esters of the compounds IV, in which A is CO, may, for example, be produced in accordance with the following reaction schemes.

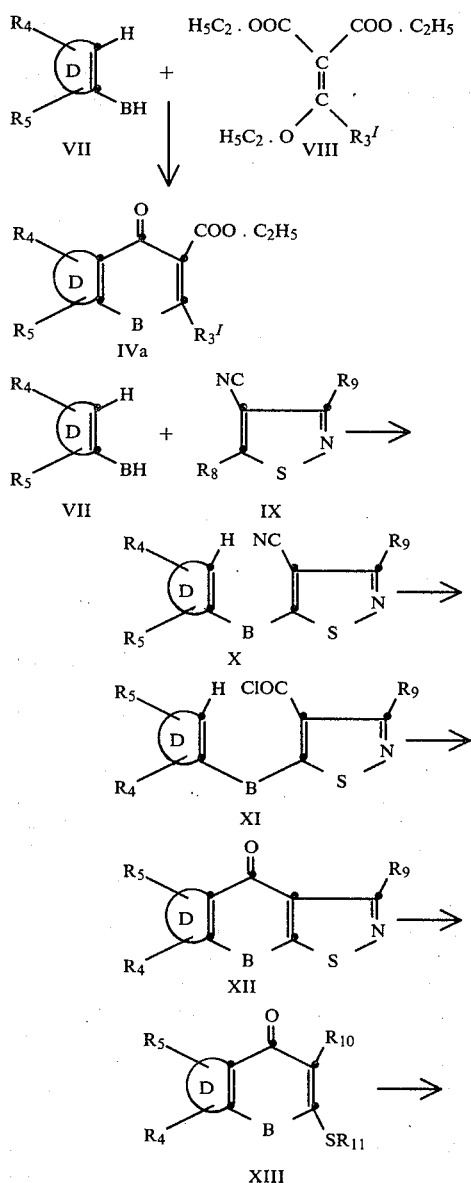

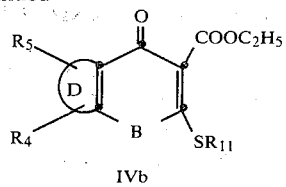

IVb in which
$R_4$, $R_5$, B and ring D are as defined above,
$R_3'$ is hydrogen or lower alkyl,
either $R_8$ and $R_9$ are each chlorine, or $R_8$ is $-SO_2CH_3$ and $R_9$ is $-OH$,
$R_{10}$ is $-CN$ or $-CONH_2$,
and $R_{11}$ is lower alkyl.

These reactions can be carried out in conventional manner, for example as illustrated in the Examples hereinafter. The corresponding ethyl esters of the compounds of formula IV in which A is $-N(R_6)CO-$ may be produced in conventional manner from the compounds of formula IVa and IVb in conventional manner, for example via the acid chloride, the acid azide and the isocyanate. The ethyl esters of the compounds of formula IV may be converted into the free acids of formula IV and other reactive derivatives in conventional manner. The compounds of formula IV may also be produced by other conventional methods, for example as hereinafter illustrated.

The compounds of formula VI are also new and may, for example, be prepared by reacting a compound of formula IV or a reactive derivative thereof, with the triethylammonium salt of an acid of formula XIV,

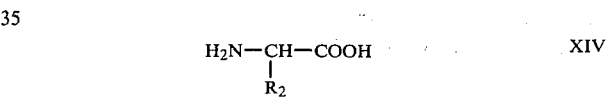

in which $R_2$ is as defined above.

This process is suitably effected in an inert organic solvent, such as a chlorinated hydrocarbon, e.g. chloroform or methylene chloride, or dimethylformamide. When a free acid of formula IV is employed, the reaction is suitably effected in the presence of a condensation agent, for example dicyclohexylcarbodiimide. The free acids of formula VI may be converted into reactive derivatives thereof in conventional manner.

The resulting compounds of formula IV and VI, and reactive derivatives thereof, may be isolated and purified using conventional techniques.

The compounds of formula I are useful as chemotherapeutic agents, in particular anti-microbial agents as indicated by their inhibiting effects against various bacteria, in particular gram-negative bacteria in vitro in the series dilution test, at concentrations of, for example, about 0.1 to 50 μg/ml and in vivo tests in the mouse. The compounds may therefore be used as antibacterially active antibiotics.

For this use, the effective dosage will of course vary depending on the particular compound employed, the mode of administration and the treatment desired. However, in general, satisfactory results can be obtained when the compounds are administered at a daily dosage of from about 10 to 500 mg/kg of animal body weight, suitably given in divided doses two to four times daily. For most large mammals, the total daily dosage is from about 1 to 6 g and dosage forms suitable for internal administration comprise about 250 to 3000 mg of the compound in admixture with a solid or liquid pharmaceutical carrier or diluent.

The compounds of formula I, in which $R_1$ is hydrogen, may be used in free acid form or in the form of their pharmaceutically acceptable salts, in particular water-soluble salts, more particularly alkali metal salts, which salt forms possess the same order of activity as the free acids. Hydrate forms may similarly be employed.

The compounds may be admixed with conventional pharmaceutically acceptable diluents or carriers and, optionally, other excipients and administered in such forms as capsules or injectable or preparations.

In one group of compounds, X signifies a radical of formula IIb. In that event $R_7$ may be hydrogen. It may also be a radical of formula IIc. Preferably it is acetoxy. X preferably, however, signifies a radical of formula IIa.

$R_1$ may be hydrogen, in which case the compounds may be in free acid form (or hydrate form). Alternatively, $R_1$ can be pivaloyloxymethyl.

A may be —N($R_6$)—CO—. $R_6$ may be hydrogen. Alternatively, $R_6$ may be lower alkyl. Preferably, however, A is —CO—.

$R_2$ may be 1,4-cyclohexadien-1-yl. Preferably, however, $R_2$ is phenyl or 4-hydroxyphenyl. More preferably, $R_2$ is 4-hydroxyphenyl.

$R_3$ can be lower alkyl. Preferably, however, it is hydrogen or lower alkylthio, more preferably hydrogen.

B can be oxygen. Alternatively, it may be sulphur.

The preferred substituents $R_4$ and $R_5$ when these are other than hydrogen, are chlorine, bromine, fluorine, lower alkyl or lower alkoxy. Preferably, however, one or both of $R_4$ and $R_5$ is hydrogen.

Ring D is preferably a benzene ring. In that event, when this is mono-substituted, the substituent preferably occupies the 6- or 8-position, and when it is disubstituted, the substituents preferably occupy the 8- and 5- or 6-positions. Alternatively, ring D may be a heterocyclic ring. Preferably this contains a simple hetero-atom, such as oxygen, sulphur or nitrogen, more preferably sulphur, and preferably is 5-membered.

The most preferred compounds of formula I are those of formula Ia,

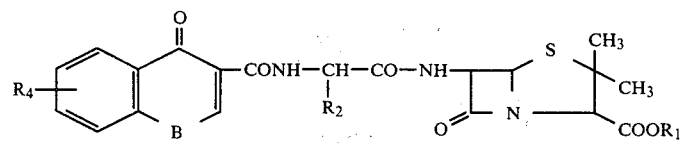

in which $R_1$, $R_2$, B and $R_4$ are as defined above.

The preferred compounds of formula Ia are those having the preferred significances for $R_1$, $R_2$, B and $R_4$ described above, in particular 6-{N-[6-fluorothiochromon-3-carbonyl]-[(4-hydroxyphenyl)glycylamino]}-3,3-dimethyl-7-oxo-4-thia-1-azabicyclo[3,2,0]-heptan-2-carboxylic acid;
and 6-{N-[chromon-4-carbonyl]-[(4-hydroxyphenyl)-glycylamino]}-3,3-dimethyl-7-oxo-4-thia-1-azabicyclo[3,2,0]-heptan-2-carboxylic acid;
and alkali metal salt forms thereof.

It will be appreciated that, by virtue of the asymmetric carbon atom (substituted by $R_2$) the compounds of the invention exist in racemic or optically active form. While the invention is not intended to be limited to any particular form of the compounds, as with known aminopenicillins and -cephalosporins, such as Ampicillin, Amoxycillin and Cephaloglycin, the D-isomers are preferred. The various forms may be obtained in conventional manner, e.g. stereo-specific synthesis from corresponding starting materials, or racemate splitting.

The following Examples illustrate the invention. All temperatures are in degrees Centigrade and all products of formula I are obtained in the form of D-isomers.

EXAMPLE 1

6-{N-[Thiochromon-3-carbonyl]-[(phenylglycyl)-amino]}-3,3-dimethyl-7-oxo-4-thia-azabicyclo[3,2-O]-heptan-2-carboxylic acid [Process (a)]

To a stirred suspension of 3 g of thiochromon-3-carboxylic acid in 50 ml of methylene chloride are added, dropwise, at 0°, 1.97 ml of triethylamine and then 1.07 ml of thionyl chloride. This solution is added simultaneously with 2.96 ml of triethylamine to a cooled (−30° C.) mixture of 5.85 g of Ampicillin trihydrate and 3.94 ml of triethylamine in 110 ml of methylene chloride, which contains 25 g of 4 Å molecular sieves (which can, however, be removed prior to addition of the acid chloride solution), dropwise. After 24 hours reaction at −20°, the molecular sieves are removed (if not already removed), the mixture is evaporated in vacuo and residue is dissolved in water. The solution is adjusted to pH 7 with 1.2 g of $NaHCO_3$ and extracted four times with diethyl ether. The aqueous phase is brought to pH 1.5 at 10° with 6 NHCl and the precipitate is collected and dried. The resulting free acid form of the heading compound is dissolved in 50 ml of tetrahydrofuran and there is added at 6° 7 ml of a 2 M potassium ethylhexanoate-isopropanol solution. The precipitate is washed well with tetrahydrofuran and chloroform to obtain the potassium salt form of the heading compound, m.p. 214°–218°.

EXAMPLE 2

6-{N-[Thiochromon-3-carbonyl]-[phenylglycyl)-amino]}-3,3-dimethyl-7-oxo-4-thia-azabicyclo[3,2-O]-heptan-2-carboxylic acid [Process a)]

67.71 g of Ampicillin trihydrate are suspended in 1115 ml of methylene chloride and 260 g of 4 Å molecular sieves and 36.86 ml of triethylamine are added. The mixture is stirred at room temperature for 2 hours and the molecular sieves are removed. To the resulting mixture is added 18.43 ml of triethylamine and then, dropwise, with stirring, at −30°, a solution of 30 g of thiochromon-3-carboxylic acid chloride in 600 ml of methylene chloride. After 17 hours at −20°, the solvent is removed in vacuo and the residue is taken up in 7 l of water at +10°. The solution is adjusted to pH 7.0 with 1 N HCl and the mixture is extracted with diethyl ether. The aqueous phase is adjusted to pH 1.5 at +10° with 6 N HCl and the resulting precipitate is washed free of HCl and dried in vacuo to obtain the free acid form of the heading compound, m.p. 155°–162°, 60 g of this are dissolved in 2 l of water with 8.9 g of $NaHCO_3$. The solution is filtered to remove insolubles, extracted several times with diethyl ether and lypophilised for 48 hours to obtain the sodium salt form of the heading compound, m.p. 216°–219°.

EXAMPLE 3

6-{N-[Thiochromon-3-carbonyl]-[phenylglycyl]-amino]}-3,3-dimethyl-7-oxo-4-thia-azabicyclo [3,2-O]-heptan-2-carboxylic acid pivaloyloxymethyl ester [Process a)]

To a mixture of 2.64 g of Ampicilin pivaloyloxymethyl ester in 30 ml of methylene dichloride are added, dropwise, at 0°, 0.95 ml of triethylamine and then a solution of 1.3 g of thiochromon-3-carboxylic acid chloride in 40 ml of methylene dichloride. After reaction for 16 hours at +4° and 16 hours at room temperature, the mixture is evaporated in vacuo and the residue is divided several times between benzene and an aqueous sodium bicarbonate solution. The organic phase is dried with magnesium sulphate and evaporated in vacuo. The residue is chromatographed on a silica gel column with a 3% solution of isopropanol in chloroform to obtain the heading compound, m.p. 104°–108°.

EXAMPLE 4

7-{N-[6-Fluorothiochromon-3-carbonyl]-[(phenylglycyl)amino]}-3-acetoxymethyl-8-oxo-5-thia-1-azabicyclo-[4,2,O]-oct-2-en-2-carboxylic acid [Process b)]

5 Drops of trifluoroacetic acid are added to a suspension of 2.02 g of Cephaloglycin in 40 ml of methylenedichloride and the mixture is stirred at room temperature for 10 minutes. 1.12 g of bis-trimethylsilylacetamide are then added and the mixture is stirred until a clear solution is obtained. A solution of 1.21 g of 6-fluorothiochromon-3-carboxylic acid chloride in 40 ml of methylene dichloride is added, dropwise, at 10°, and, after 90 minutes reaction time, the mixture is evaporated. The residue is divided between water and ethyl acetate, and the organic phase is washed with 1 N HCl and saturated sodium chloride solution. The mixture is extracted with sodium bicarbonate and the solution is acidified with 1 N HCl. The heading compound is isolated by extraction with ethyl acetate and evaporation. M.P. 230°–240°.

The compounds set out in the following Table may be obtained in manner analogous to any one of the preceding Examples using appropriate starting materials in approximately equivalent amounts. Where a compound is obtained in a particular salt form, this is, for convenience, indicated in column $R_1$.

| Ex. | $R_1$ | $R_2$ | $R_3$ | A | B | D | | X | m.p. |
|---|---|---|---|---|---|---|---|---|---|
| 5 | K | —$C_6H_5$ | H | CO | S | F |  |  | 118–122° |
| 6 | K | " | H | CO | S | $H_3C$ |  | " | 231–236° |
| 7 | K | " | H | CO | S | Cl |  $CH_3$ | " | 230° |
| 8 | K | " | S·$C_2H_5$ | CO | S | |  | " | 210–215° |
| 9 | K | " | H | CO | S | Cl |  | " | 218–221° |
| 10 | Na | " | H | CO | S | " | | " | 220–225° |
| 11 | K | " | H | CO | S | |  Cl | " | 220° |
| 12 | K | " | H | CO | O | |  | " | 208–215° |
| 13 | K | " | H | CO | O | Cl |  | " | 220–225° |
| 14 | K | " | S·$CH_3$ | CO | O | Cl |  | " | 230° |
| 15 | Na | " | H | CO | O | $H_3C$ |  | " | 118–120° |
| 16 | Na | " | H | CO | O | Cl | (structure with Cl) | " | 235–239° |

| Ex. | R₁ | R₂ | R₃ | A | B | D | X | m.p. |
|---|---|---|---|---|---|---|---|---|
| 17 | K |  —OH | H | CO | S |  | " | 222° |
| 18 | K | " | H | CO | S |  | " | 230–235° |
| 19 | K | " | H | CO | S |  | " | 230° |
| 20 | K | " | H | CO | S |  | " | 231° |
| 21 | K | " | H | CO | S |  | " | 222–230° |
| 22 | K | " | H | CO | O |  | " | 220° |
| 23 | K | " | H | CO | O |  | " | 225–230° |
| 24 | K |  | H | CO | S |  | " | 225–229° |
| 25 | K | " | H | CO | S |  | " | 215° |
| 26 | K | —C₆H₅ | H | CO | S |  | " | 200–210° |
| 27 | K |  —OH | H | CO | S | " | " | 218–220° |
| 28 | K | —C₆H₅ | H | CO | O |  | " | 240–245° |
| 29 | Na | " | H | CO | O |  | " | 233–237° |
| 30 | Na |  —OH | H | CO | S |  | " | 232° (decom.) |
| 31 | H | " | H | CO | S | " | " | 178–180° |

The starting materials of formula IV employed in the preceding Examples may be produced as follows:

A. Thiochromon-3-carboxylic acid chloride (Examples 1, 2, 3, 17, 24)

(a) Mercaptophenylmethylenemalonic acid diethyl ester

A mixture of 440 g of thiophenol and 864 g of ethoxymethylenemalonic acid diethyl ester is warmed at 140° for 48 hours. The mixture is evaporated under pressure and the residue is distilled under high vacuum to obtain the heading compound, b.p. 185°, $2 \times 10^{-4}$ Torr.

(b) 3-Ethoxycarbonylthiochromon 380 g of polyphosphoric acid are mixed at 75° over a period of 20 minutes with 50 g of the product of step (a). The mixture is stirred for 15 minutes, poured onto ice/water and extracted 3 times with diethyl ether. The ether phase is shaken once with bicarbonate solution and evaporated. The residue is crystallized from benzene/hexane (7:3) to obtain the heading compound, m.p. 65°–70°.

(c) Thiochromon-3-carboxylic acid 37 g of the product of step (b) are maintained in 300 ml of 50% sulphuric acid for 16 hours at 80°. The residue is filtered and washed with water and ethanol to obtain the heading compound, m.p. 230°–233°.

(d) Thiochromon-3-carboxylic acid chloride 30.93 g of the product of step (c) are boiled in 310 ml of thionyl chloride under reflux for 1 hour. The mixture is evaporated to dryness and the residue is filtered, washed with n-hexane and dried in vacuo to obtain the heading compound, m.p. 135°–140° C.

In manner analogous to Example (Aa) to (c) described above, the following compounds of formula IV may be obtained:

6-chlorothiochromon-3-carboxylic acid, m.p. 191°–208° [for Examples 9, 10, 21];

8-chlorothiochromon-3-carboxylic acid, m.p. 192°–200° [for Examples 11, 19];

6-fluorothiochromon-3-carboxylic acid, m.p. 273° [for example 5, 18];

6-methylthiochromon-3-carboxylic acid, m.p. 218°–220° [for Examples 6, 20, 25];
5-chloro-8-methoxythiochromon-3-carboxylic acid, m.p. 262°–264° [for Example 7];
6-methoxythiochromon-3-carboxylic acid, m.p. 205° [for Example 26, 27].

B. 2-Ethylmercaptothiochromon-3-carboxylic acid [for Example 8]

(a) 3-Chloro-5-mercaptophenylisothiazol-4-carboxyl acid amide 65 g of 3-chloro-4-cyano-5-mercaptophenylisothiazol are added to 200 ml of concentrated sulphuric acid and the mixture is warmed to 80° quickly and then allowed to stand at room temperature for 18 hours. The mixture is shaken on ice/water and the precipitate is filtered off and washed with water.

(b) 3-Chloro-5-mercaptophenylisothiazol-4-carboxylic acid 57 g of the product of step (a) are dissolved in 1.3 l of sulphuric acid (77 vol %) and the mixture is cooled to 5°. Over a period of 10 minutes, 33.2 g of sodium nitrite in 100 ml of water are introduced under the surface and the mixture is stirred at 30° for 90 minutes and at 60° for 15 minutes. The mixture is mixed, under cooling, at room temperature, with 1.5 l of water and the resulting precipitate is filtered and washed with water to obtain the heading compound, m.p. 150°–160°.

(c) 3-Chloro-5-mercaptophenylisothiazol-4-carboxylic acid chloride 50 g of the product of step (b) are dissolved in 500 ml of thionyl chloride and the mixture is held at 50° for 20 hours. The thionyl chloride is removed at 12 mm to obtain the heading compound.

(d) 3-chloroisothiazolo[4,5-b]thiochromon

To a refluxing mixture of 1 l of carbon disulphide and 99 g of aluminium chloride is added, over 1 hour, 39.7 g of the product of step (c) in 250 ml of carbon disulphide, dropwise. The mixture is refluxed for 2 hours and the carbon disulphide decanted off. The residue is digested with methanol/water and, after filtration, the residue is shortly boiled with methanol/water, filtered and washed with methanol to obtain the heading compound, m.p. 218°–220°.

(e) 2-Ethylmercapto-3-cyanothiochromon 4.7 g of the product of step (d) in 50 ml of dimethylformamide are heated to 60° and mixed, dropwise, with 10 ml of a 0.01 M $NaHCO_3$ solution. After addition of 20 ml of ethyl iodide, the mixture is allowed to stand for 18 hours and the resulting precipitate is filtered and washed to obtain the heading compound, m.p. 175°–179°.

(f) 2-Ethylmercapto-3-cyanothiochromon-3-carboxylic acid amide 0.5 g of the product of step (e) in 10 ml of concentrated sulphuric acid are warmed at 50° for 38 hours. The mixture is shaken on ice/water, and stirred for 10 minutes and the resulting precipitate is separated and washed with water to obtain the heading compound, m.p. 165°–168°.

(g) 2-Ethylmercapto-3-cyanothiochromon-3-carboxylic acid 0.3 g of the product of step (f) are dissolved in 5 ml of 80% sulphuric acid and mixed with 0.15 g of sodium nitrite in 1 ml of water. The mixture is stirred for 40 minutes at 50°–55°, shaken on water and the resulting precipitate is separated and washed with water. The crude product is recrystallised from methanol to obtain the heading compound, m.p. 213°–217°.

In manner analogous to Example (Ba) to (g). Using appropriate starting materials in approximately equivalent amounts, the following compound may be obtained: 6-chloro-2-methylthiochromon-3-carboxylic acid, m.p. 265° [for Example 14].

C. 6,8-Dichlorochromon-3-carboxylic acid [for Example 16]

(a) 3-Cyano-6,8-dichlorochromon 15 g of 6,8-dichlorochromon-3-aldehyde, 5.43 g of hydroxylamine hydrochloride, 7.55 g of sodium formamide and 100 ml of formic acid are mixed at room temperature and refluxed for 4 hours. After a further 18 hours at room temperature, the precipitate is separated and the filtrate is poured into 1 l of water. The resulting precipitate is filtered off and washed twice with water and twice with ethanol to obtain the heading compound, m.p. 150°.

(b) 6,8-Dichlorochromon-3-carboxylic acid 8 g of the product of step (a) are dissolved in 30 ml of conc. sulphuric acid and the solution is allowed to stand for 18 hours at room temperature. After addition of 90 m of conc. and 200 ml of 80% sulphuric acid, 5.5 g of sodium nitrite in 10 ml of water are introduced under the liquid surface at 5°–10°. The mixture is stirred at 10° for 15 minutes and at 70° for 30 minutes and then poured into 1 l of water. The resulting precipitate is separated, washed 3 times with water and twice with ethanol, to obtain the heading compound, m.p. 196°, which can be crystallised from acetic acid.

D. 6-Bromochromon-3-carboxylic acid [for Example 28]

(a) 6-Bromochromon-3-aldehyde 110 g of 2-Hydroxy-5-bromoacetophenone are dissolved in 1 l of dried dimethyl formamide. Under stirring, 183 g of $POCl_3$ are added slowly and the mixture is stirred overnight. The resulting precipitate is separated, quickly washed with dimethyl formamide and dried. The crystals are taken up in 1 l of water and the mixture stirred for 30 minutes and filtered. The residue is washed 4 times with water and once with ethanol and dried to obtain the heading compound, m.p. 190°–193°.

(b) 3-Cyano-6-bromochromon 85 g of the product of step (b) are dissolved at room temperature in 600 ml of formic acid and mixed with 30 g of hydroxylamine hydrochloride and 42.5 g of sodium formate. The mixture is stirred, warmed to boiling, refluxed for 4 hours and allowed to cool overnight. The precipitate is separated, suspended in 200 ml of water and stirred for 20 minutes. The mixture is filtered and the residue washed with water and ethanol, and dried to obtain the heading compound, m.p. 193°–200°.

(c) 6-Bromochromon-3-carboxylic acid 26 g of the product of step (b) are stirred overnight in 150 ml of conc. sulphuric acid at room temperature. The mixture is then diluted with 10 ml of water and cooled to 0°. Under stirring, a solution of 15 g of sodium nitrite in 30 ml of water is introduced slowly under the liquid surface, the temperature being maintained by cooling at 15°. After addition, the mixture is warmed at 70° for 1 hour and poured over ice and the precipitate is suction filtered off, suspended in 600 ml of acetone, refluxed, hot-filtered and the filtrate then evaporated on a rotary evaporator. The residue is recrystallised from chloroform, to obtain the heading compound, m.p. 260°–264°.

E. Thieno[2,3-a]thiopyron(4)-5-carboxylic acid [For Examples 30, 31]

(a) 3-(2-Mercapto)thienylpropionic acid 14.28 g of sodium are dissolved in 300 ml of dried ethanol. At the same time, 35 g of 2-mercaptothiophene are dissolved in 50 ml of dried ethanol and poured, under argon, onto the sodium ethoxide. After 15 minutes stirring, 47.4 g of 3-bromopropionic acid are added. The mixture is stirred for 3 hours at room temperature and then poured into 500 ml of 2 N HCl with stirring. This mixture is then shaken with 500 ml of diethyl ether. The ether phases are extracted with 700 ml of saturated $NaHCO_3$ solution and the aqueous phase is acidified to pH 2, extracted with chloroform, dried with sodium sulphate and evaporated on a rotary evaporator. The oily residue is dissolved in a little diethyl ether and mixed with n-pentane. The heading compound crystallises out on cooling and seeding, m.p. 43°–44°.

(b) Thieno[2,3-a]thiopyron(4)

41 g of 2-(2-Mercapto)thienylpropionic acid are dissolved in 100 ml of polyphosphate ester solution (obtained by dissolving 60 g of $P_2O_5$ in 60 ml of diethyl ether and 120 ml of chloroform and refluxing for 24 hours). The mixture is refluxed 2½ hours, and evaporated to remove the solvent. The residue is taken up in 300 ml of ethyl acetate and extracted with water until such time as the water is no longer coloured red. The resulting ethyl acetate phase is dried over sodium sulphate and evaporated to dryness in vacuo. The oily residue crystallises in the cold with rubbing. The precipitate is filtered with a mixture of diethyl ether and petroleum ether and then dissolved in 70 ml of ethanol (96%) with heating. The mixture is cooled and precipitated with water to obtain the heading compound, m.p. 54°–58°.

(c) (Thieno[2,3-a]-5,6-dihydrothiopyrone(4)-5-yl)glyoxylic acid ethyl ester 0.805 g of Sodium are dissolved in 30 ml of absolutely dry ethanol and the mixture is cooled to 0°. In the meantime, 5.98 g of thieno[2,3-a]thiopyron(4) and 5.08 g of oxalic acid diethyl ester are dissolved in 9 ml of dry ethanol and this solution is added dropwise to the cooled sodium ethoxide. The mixture is stirred for 30 minutes at 0° and then for 16 hours at room temperature and then poured onto 150 ml of pH 6.5 buffer solution. The mixture is acidified slightly with 1 N HCl and extracted with 400 ml of diethyl ether. The ether phase is washed once with saturated potassium chloride solution, dried over sodium sulphate and evaporated in vacuo to remove the solvent completely. The heading compound remains as an intense yellow oil which is employed directly in the next step.

(d) Thieno[2,3-a]thiopyron(4)-5-yl)glyoxylic acid ethyl ester 11.205 g of sodium hydride are suspended in 750 ml of absolute tetrahydrofuran and the mixture is cooled to 0°. A solution of 67.3 g of (thieno[2,3-a]-5,6-dihydrothiopyron(4)-5-yl)glyoxylic acid ethyl ester in 100 ml of absolute tetrahydrofuran is added dropwise. A solution of phenylselenylbromide (obtained by dissolving 42.76 g of diphenyl diselenide in 100 ml of absolute tetrahydrofuran and adding dropwise with ice cooling 21.89 g of bromine) is poured into the mixture. The resulting mixture is stirred for 1½ hours with ice cooling and then poured into a mixture of 1.2 l of diethyl ether, 600 ml of saturated sodium bicarbonate solution and a little ice. The ether phase is separated and the aqueous phase extracted again with ether. The ether phases are collected and washed with sodium chloride solution, dried over sodium sulphate and concentrated, and the resulting precipitate is filtered, m.p. 118°–125°.

54.93 g of this precipitate are dissolved in 400 l of chloroform and to this solution is added, dropwise, with cooling, a solution of 32.8 ml of 30% $H_2O_2$ in 32.3 ml of water. The mixture is stirred for a further 10 minutes and then stirred into a mixture of 300 ml of methylene dichloride and 130 ml of 10% soda solution. The organic phase is separated and extracted again with methylene dichloride. The combined organic phases are washed with saturated sodium chloride solution, dried over sodium sulphate and evaporated in vacuo. The resulting light oil crystallises immediately on cooling to obtain the heading compound, m.p. 109°–110°.

(e) Thieno[2,3-a]thiopyron(4)-5-carboxylic acid 18 g of the product of step (b) are dissolved in 700 ml of acetic acid and 40.5 ml of 30% $H_2O_2$ is added. The mixture is warmed for 4 hours at 80% and then evaporated in vacuo. The residue is taken up in aqueous sodium bicarbonate solution and extracted once with methylene dichloride and once with ethyl acetate. The aqueous phase is acidified to pH 1 and the resulting precipitate is filtered off, washed with water and dried in vacuo. The product is recrystallised from 96% ethanol to obtain the heading compound, m.p. 203°–213° C.

The following Example illustrates the production of starting materials of formula VI:

N-[6-Fluorothiochromon-3-carbonyl]phenylglycin (for Example 4)

3.63 g of D(−)-α-phenylglycine are dissolved in 100 ml of water and 4 g of sodium carbonate. With vigorous stirring, a solution of 4.85 g of 6-fluorothiochromon-3-carboxylic acid chloride in 160 ml of methylene chloride are added, and, after 1¾ hours reaction, the aqueous phase is adjusted to pH 2 with 2 N HCl. The crystalline precipitate is washed and crystallised with methanol to obtain the heading compound, m.p. 212°–221°.

The corresponding compounds of formula 6, required for production of the compounds of Examples 1 and 5 to 31 may be produced in analogous manner, employing appropriate starting materials in approximately equivalent amounts.

The compounds of formula I, indicated in the following table, may also be produced in manner analogous to that of Examples 1 to 4, employing appropriate starting materials in approximately equivalent amounts.

| Ex. | R₁ | R₂ | R₃ | A | B | D | X |
|---|---|---|---|---|---|---|---|
| 31 | Na | —⟨phenyl⟩ | CH₃ | —NHCO— | O | ⟨phenyl dimethyl⟩ | —CH₂—C(CH₃)= |
| 32 | K | —⟨phenyl⟩ | CH₃ | —CO— | O | HO—⟨phenyl dimethyl⟩ | —CH₂—C(CH₃)= |
| 33 | H | —⟨phenyl⟩—OH | H | —NHCO— | S | HOOC—⟨phenyl dimethyl⟩ | CH₃COOCH₂<br>\|<br>—CH₂—C= |
| 34 | H | —⟨phenyl⟩ | CH₃ | —NHCO— | S | CH₃—⟨phenyl dimethyl⟩ | —CH₂—C(CH₃)= |
| 35 | t-but-COOCH₂— | —⟨phenyl⟩ | CH₃ | —NHCO— | S | ⟨phenyl with CH₃OCOCH₂⟩ | =C(CH₃)₂ |
| 36 | K | —⟨phenyl⟩ | H | CO | O | CH₃OCO—⟨phenyl⟩ | =CH(CH₃)₂ |

What is claimed is:

1. A compound of the formula

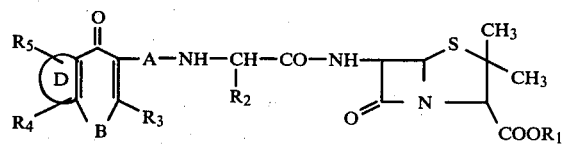

wherein

R₁ is hydrogen or pivaloyloxymethyl, and
R₂ is 4-hydroxyphenyl or 1,4-cyclohexadien-1-yl, and
R₃ is hydrogen, lower alkylthio, and
R₄ and R₅ independently represent hydrogen, lower alkyl, hydroxy, lower alkoxy, carboxyl, lower alkoxycarbonyl, lower alkoxycarbonylmethyl or halogen, and
A is the group

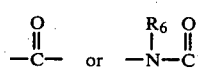

in which R₆ is hydrogen or lower alkyl, and
B is oxygen or sulphur, and
D is a 5- or 6-membered, unsaturated ring, which may contain one or more nitrogen, oxygen or sulphur group,
or a pharmaceutically acceptable salt thereof when R₁ is hydrogen.

2. A compound of claim 1 wherein R₂ is 4-hydroxyphenyl.

3. A compound of claim 1 wherein R₂ is 1,4-cyclohexadiene-1-yl.

4. A compound of the formula

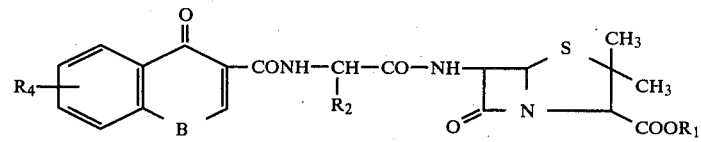

wherein
B is oxygen, and
R₁, R₂ and R₄ are as defined in claim 1, or a pharmaceutically acceptable salt thereof when R₁ is hydrogen.

5. A compound of the formula

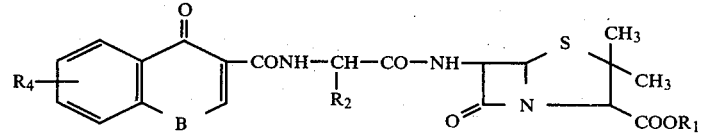

wherein
B is sulphur and
R₁, R₂ and R₄ are as defined in claim 1, or a pharmaceutically acceptable salt thereof when R₁ is hydrogen.

6. The compound of claim 1, which is 6-{N-[6-fluoro-thiochromon-3-carbonyl]-[(4-hydroxyphenyl)-glycylamino]}-3,3-dimethyl-7-oxo-4-thia-1-azabicyclo-[3,2,0]-hepten-2-carboxylic acid, and salt thereof.

7. The compound of claim 1, which is 6-{N-[chromon-3-carboxyl]-[(4-hydroxyphenyl)glycylamino]}-3,3-dimethyl-7-oxo-4-thia-1-azabicyclo-[3,2,0]-hepten-2-carboxylic acid, and salt thereof.

8. A method of combatting bacteria comprising administrating to a subject in need of such treatment an effective amount of a compound of claim 1, or a pharmacologically acceptable salt thereof.

9. A pharmaceutical composition which comprises an anti-bacterial effective amount of a compound of claim 1, or a pharmacologically acceptable salt thereof, in association with a pharmacologically acceptable diluent or carrier.

* * * * *

UNITED STATES PATENT AND TRADEMARK OFFICE
CERTIFICATE OF CORRECTION

PATENT NO. : 4,320,133

DATED : March 16, 1982

INVENTOR(S) : Helmut Hamberger; Peter Stutz; Dieter Scholz; Hans Fliri

It is certified that error appears in the above-identified patent and that said Letters Patent is hereby corrected as shown below:

Title page, Item [30]; change "[SE] Sweden" to -- [CH] Switzerland --.

Column 1, line 4 (line 1 beneath the title); after "of", delete -- copending --.

Column 14, line 24; after "400", change "l" to -- ml --.

Column 15, line 52; after the first occurrence of a comma, insert -- lower alkyl or --.

Column 16, line 57; change "mon-3-carboxyl]" to -- mon-3-carbonyl] --.

Signed and Sealed this

Twenty-second Day of February 1983

[SEAL]

Attest:

GERALD J. MOSSINGHOFF

Attesting Officer     Commissioner of Patents and Trademarks